US008517938B2

(12) United States Patent
Eisenhardt et al.

(10) Patent No.: US 8,517,938 B2
(45) Date of Patent: Aug. 27, 2013

(54) MEDICAL SYSTEM HAVING CONSUMABLES MONITORING

(75) Inventors: Christoph Eisenhardt, Mannheim (DE); Volker Huellen, Mannheim (DE); Oliver Kube, Worms (DE); Josef Roeper, Neuhofen (DE); Friedrich Ziegler, Stuttgart (DE)

(73) Assignee: Roche Diagnostics Operations, Inc.

( * ) Notice: Subject to any disclaimer, the term of this patent is extended or adjusted under 35 U.S.C. 154(b) by 466 days.

(21) Appl. No.: 12/767,579

(22) Filed: Apr. 26, 2010

(65) Prior Publication Data

US 2011/0112384 A1    May 12, 2011

Related U.S. Application Data

(63) Continuation of application No. PCT/EP2008/064380, filed on Oct. 23, 2008.

(30) Foreign Application Priority Data

Oct. 24, 2007    (EP) .................................... 07119134

(51) Int. Cl.
*A61B 5/00*    (2006.01)
*C12Q 1/54*    (2006.01)
*G08B 1/08*    (2006.01)

(52) U.S. Cl.
USPC ............. 600/300; 600/309; 600/583; 435/14; 340/539.12

(58) Field of Classification Search
USPC ........ 600/300, 309, 310, 316, 347; 422/68.1; 435/4, 14; 340/539.12; 702/19
See application file for complete search history.

(56) References Cited

U.S. PATENT DOCUMENTS

| 5,318,584 A | 6/1994 | Lange et al. |
| RE35,803 E | 5/1998 | Lange et al. |

(Continued)

FOREIGN PATENT DOCUMENTS

| DE | 10237602 A1 | 3/2004 |
| EP | 0565970 B1 | 9/1997 |

(Continued)

OTHER PUBLICATIONS

FDA U.S. Food and Drug Administration Press Release, "FDA Announces New Initiative to Protect the U.S. Drug Supply Through the Use Of Radiofrequency Identification Technology", P01-103, Nov. 15, 2004. http://www.fda.gov/bbs/topics/news/2004/NEW01133.html.

(Continued)

*Primary Examiner* — Eric Winakur
(74) *Attorney, Agent, or Firm* — Roche Diagnostics Operations, Inc.

(57) ABSTRACT

The invention proposes a medical system which comprises a central control unit which is set up to display at least one diagnostic measured value using a display element. The medical system also comprises at least one invasive unit, wherein the invasive unit has at least one invasive consumable. The invasive consumable is set up to invasively intervene in a tissue of a patient. The invasive unit has at least one contactlessly readable electronic identifier for storing at least one piece of information. The central control unit is set up to electronically read the at least one piece of information in the electronic identifier. The central control unit and the invasive unit are functionally independent of one another such that the respective function of the central control unit and of the invasive unit can be performed independently of the presence of the respective other unit.

29 Claims, 3 Drawing Sheets

(56) References Cited

U.S. PATENT DOCUMENTS

| | | | |
|---|---|---|---|
| 5,989,917 | A | 11/1999 | McAleer et al. |
| 6,379,317 | B1 | 4/2002 | Kintzig et al. |
| 6,482,185 | B1 | 11/2002 | Hartmann |
| 6,641,533 | B2 * | 11/2003 | Causey et al. ............ 600/300 |
| 7,263,501 | B2 * | 8/2007 | Tirinato et al. ............ 705/28 |
| 8,034,294 | B1 * | 10/2011 | Goldberg ............ 422/68.1 |
| 2003/0004403 | A1 | 1/2003 | Drinan et al. |
| 2004/0034318 | A1 | 2/2004 | Fritz et al. |
| 2004/0138688 | A1 | 7/2004 | Giraud |
| 2005/0187444 | A1 | 8/2005 | Hubner et al. |
| 2006/0182656 | A1 | 8/2006 | Funke et al. |
| 2007/0041244 | A1 | 2/2007 | Chih et al. |
| 2007/0232879 | A1 | 10/2007 | Brister et al. |
| 2007/0232958 | A1 | 10/2007 | Donofrio et al. |

FOREIGN PATENT DOCUMENTS

| | | |
|---|---|---|
| EP | 1574855 A1 | 9/2005 |
| EP | 1333756 B1 | 12/2005 |
| EP | 1669020 A1 | 6/2006 |
| EP | 1043037 B1 | 11/2006 |
| EP | 1776975 A2 | 4/2007 |
| EP | 1032307 B1 | 5/2007 |
| EP | 1825806 A2 | 8/2007 |
| EP | 1352611 B1 | 11/2008 |
| GB | 2331935 B | 10/2002 |
| WO | 99/27854 A1 | 6/1999 |
| WO | 01/14912 A1 | 3/2001 |
| WO | 03/082091 A2 | 10/2003 |
| WO | 2004/088037 A1 | 10/2004 |
| WO | 2005/067797 A1 | 7/2005 |
| WO | 2006/065754 A2 | 6/2006 |

OTHER PUBLICATIONS

Public Global Roche Statement on Counterfeiting, May 2006.
Hamburger Abendblatt, "Fraud involving counterfeit lancets", Dec. 2005.
International Preliminary Report on Patentability from corresponding PCT/EP2008/064380 (English Translation), mailed Sep. 10, 2010.
International Search Report from corresponding PCT/EP2008/064380 (English), mailed Jan. 21, 2009.
International Search Report from corresponding PCT/EP2008/064380 (German Language), mailed Jan. 21, 2009.
International Preliminary Report on Patentability from corresponding PCT/EP2008/064380 (German Language), mailed Feb. 11, 2010.

* cited by examiner

MEDICAL SYSTEM HAVING CONSUMABLES MONITORING

CLAIM OF PRIORITY

The present application is a continuation based on and claiming priority to PCT Application No. PCT/EP2008/064380, filed Oct. 23, 2008, which claims the priority benefit of European Application No. 07119134.0, filed Oct. 24, 2007, each of which are hereby incorporated by reference in their respective entireties.

TECHNICAL FIELD OF THE INVENTION

The invention relates to a medical system which comprises a central control unit and an invasive unit having at least one invasive consumable. The invention also relates to a method for monitoring a medical system. Such medical systems and methods for monitoring the medical systems are used particularly in the field of medical diagnostics and medical therapeutics, for example in the course of a homecare program for diabetes patients or in the course of clinical diagnostics or therapeutics in hospitals and care homes. Other fields of use are also possible.

BACKGROUND

For different illnesses, the concentrations of various analytes in body fluids of the patient need to be regularly monitored. By way of example, the monitoring of the blood glucose concentration is an essential part of the daily routine for diabetics. In this case, the blood glucose concentration usually needs to be determined quickly and reliably several times during the day in order to be able to take appropriate medical measures if necessary.

Besides diagnostics, appropriate medication also plays a crucial part. By way of example, to compensate for fluctuations in the blood glucose concentration, a diabetic needs to take insulin medication matched to the measured blood glucose concentrations.

So as not to restrict the daily routine of patients, particularly diabetics, any more than is necessary, appropriate mobile devices are frequently used both for diagnostics and for medication which should be easy to transport and to handle, so that the measurement or the medication can be taken at work, while out and about or in one's free time, for example.

For the diagnostics, for example for determining a particular analyte in body fluids (for example in blood), particularly for determining blood glucose or lactate, it is necessary to obtain an adequate amount of this body fluid. To obtain a blood sample, for example, or another sample of a body fluid, a lancet is usually used to pierce the patient's skin on selected body parts, for example on the finger pad or the ear lobe. To make obtaining blood convenient, to control the depth of prick and to minimize the pain, various manufacturers supply lancing devices which insert a lancet in controlled and guided fashion into a skin part. Such a lancing device is described in EP 0 565 970 B1, for example. These lancing devices can also be mechanically connected in reversible fashion to a measuring device which is used to determine the analyte concentration, as described in EP 1 032 307 B1, for example. Despite this mechanical coupling, the lancing device and the measuring device continue to be units operating independently of one another, however, and together form a medical system.

The lancets are usually disposable products which, by way of example, comprise a highly sharpened metal pin and an integrally molded plastic holder which produce the connection to the lancing device. Other embodiments of lancets are also possible, however, for example lancets in the form of sharp edges or spines which are moved by the lancing device as appropriate.

On account of their generally comparatively simple design, lancets can easily be replicated or imitated, however. Frequently inadequate fits, inferior materials or lack of sterilization mean that replicated lancets or other consumables can cause considerable health risks and injuries during use, however. This applies particularly to invasive consumables, that is to say consumables which are set up to intervene in a body tissue of a patient (like lancets). A further drawback of such imitated consumables is that inadequate fits can sometimes damage the peripheral devices used. Furthermore, imitated consumables and replicas result in considerable financial losses for the effected companies and, in the case of malfunctions, a damage to reputation.

The lancets or other types of consumables may be arranged in a magazine, so that the user does not have to change the lancet prior to each use of a lancing device but rather replaces the magazine only at relatively long intervals of time, when all the lancets contained in said magazine have been used up. Such a system is described in EP 1 333 756 B1, for example. A product example of a lancing device with a lancet magazine is the lancing device "Accu-Chek Multiclix" from Roche Diagnostics GmbH. Lancet magazines can also be replicated with the aforementioned consequences for the affected companies. Lancets, lancet magazines and lancing devices are usually purely mechanical parts without electrical or analytical functions.

Similar problems to those described above for lancets also arise with other types of consumables. By way of example, it is also a fundamental possibility for consumables which have an analytical function (for example test elements or subcutaneous sensors), consumables for medication (for example cannulas, catheters or the like) or other types of consumables to be affected. Consumables in general are frequently also referred to as "disposables" in diagnostics.

From other areas of medicine, numerous different apparatuses and methods are known which are intended to ensure that medicaments or medical devices cannot be replicated. Today, for example, a large number of different technical solutions are used which include, by way of example, holograms or electronic identifiers, in particular radio frequency tags (RFID tags), which can be affixed to medicament packages, for example. RFID technology as an example of electronic identifiers comprises contactless identification by means of radio waves. The information in such an RFID tag, which is also called an RFID label and which contains an electronic chip, is usually transmitted wirelessly by radio at different frequencies to a reader which can then display and/or store the information. The use of RFID tags is advocated by the American health authority FDA to enhance the prevention of replication in the pharmaceutical industry, for example.

Electronic identifiers which can store a piece of electronically readable information are generally available in numerous designs. Besides designs which contain a silicon chip and an antenna (which is usually referred to as an RFID tag), for example, RFIDs are also known which are based on organic electronics (for example semi conductive or conductive polymers). In addition, inexpensive, printed designs of electronic identifiers are also known. These designs, also known as "chipless identifiers", involve the piece of information being encrypted in an electrically conductive bar code, for example, and it then being able to be read contactlessly via numerous antennas in a reader. An example of such a design is disclosed in WO 2004/088037 A1.

The methods for enhancing the prevention of replication which are known from the prior art have some drawbacks, shortcomings and challenges of a technical nature in practice. Most methods require a complex reader and display device for checking the authenticity of the protected medical devices. This is usually not mobile and/or too expensive to be available to every user. In the case of the known methods, the user is therefore usually not able to recognize independently replicated medical devices, such as consumable materials.

Furthermore, a medical system is usually made up of a plurality of individual components which, even if some of said components can be integrated in a common housing or mechanically connected to one another, usually perform their functions independently of one another. An example is the cited lancing devices, which almost always have a purely mechanical functionality and which are not functionally correlated to a measuring device, which in turn is used for measuring an analyte concentration in a blood sample produced by means of the lancing device. To recognize replicated consumables, a user would therefore need to carry a separate reader which can read the identifiers, even in the case of the methods cited above for identifying these consumables. This is barely possible in many cases for reasons of space, however, and also represents increased cost outlay.

In addition, by way of example, purely mechanically operating peripheral devices, such as purely mechanical lancing devices, usually have no display option for displaying the information in the identifiers of the consumables. This means that the user cannot be provided with any information about said consumables, such as lancets. Even if a peripheral device, such as a lancing device, is mechanically coupled to a measuring device with a display option, as is the case with the commercially available products Accu-Chek Softclix Plus and Accu-Chek Compact Plus, for example, both devices are usually nevertheless functionally decoupled from one another, which means that the user usually has no way of reliably recognizing replicas, as previously, on account of a lack of explicit identification features of the consumables. Overall, it is therefore usually impossible for a user to himself recognize whether he is using a safe medical device or whether he is using a replicated lancet or a replicated lancet magazine or other types of unsuitable consumable materials.

Furthermore, current technical solutions for preventing replication have the drawback that they themselves can be replicated in many cases. This is the case with holograms, for example.

Other types of information transmission with other types of identifiers within units in medical engineering devices are also known and are presented in the examples below. The parts of the units are in this case generally functionally dependent on one another, which distinguishes the prior art described from the invention described below.

An example of information transmission between parts of a unit which are functionally dependent on one another is described in EP 1 574 855 A1, for example. These blood sugar measuring devices involve batch specific information being transmitted to the unit's measuring device from a test carrier optically or by means of wireless electronics (for example see DE 102 37 602 A1).

EP 1 043 037 A2 describes an injection apparatus with a pen which contains an expressible injection. The dosage when the injection is expressed is adjusted using a dosage adjustment apparatus. For visually impaired people, it is very difficult to adjust the dosage. An external display device is therefore provided which can be attached to the pen. Contacts and mating contacts are used to transmit a piece of information about the dosage to the display device and to display it on a large format display. In this case, it is also proposed that the pen be equipped with a coding, which can be recognized by the display device, in the form of elevations or depressions so that the display device always knows with which pen or pen type it is collaborating. The injection apparatus described in EP 1 043 037 A2 is tailored very specifically to one particular unit, however, and is therefore inflexible in the face of changing combinations of the individual components. Recognition of the pen requires a direct mechanical coupling to be made, and the system is inoperative if a pen which cannot be recognized by the display device is used.

EP 1 352 611 describes a measuring unit with a container for test elements, which container may be provided with an information chip in order to send information about the number and calibration data of test strips to a measuring device of the unit. In these systems, the RFID tag is used to forward necessary information to the measuring device, which information would otherwise have to be transferred to the measuring device using what is known as a ROM key or other information sources or else manually, for example, in order to allow the test strips to be evaluated. Accordingly, the RFID tag in the dispenser, as described in US 2006/0182656 and EP 1 352 611, is merely a variant for known methods and apparatuses in order to provide the measuring device with information which is necessary for the measurement, without which meaningful measurement or evaluation of the measurement would be impossible or possible only with difficulty. In this example of the prior art, the RFID technology is used to transmit information between the parts of a measuring unit.

US 2004/0138688 describes the identification of a lancet in which the identification is in the form of a bar code. However, this bar code does not have electronic information and therefore cannot be identified by a device which does not make direct optical contact with the consumable.

US 2007/0232879 A1 describes devices and methods for determining an analyte concentration. These involve the use of a mounting unit which is used for mounting a transdermal sensor. This mounting unit comprises, inter alia, an electronics unit which comprises, inter alia, an RFID identifier for identifying the sensor. Signals from said RFID identifier can be picked up by a receiver unit.

US 2002/0004403 A1 describes a unit which comprises a measuring head (BioInterface Head, BIH) with sensors for monitoring physiological parameters and which comprises a control module (Communication and Control Module, CCM) which actuates and reads the measuring head. In this case, a plurality of sensors may also be provided. Wireless data transmission can take place between BIH and CCM. In addition, identification management is also proposed which involves the interchange of information about the sensor type, for example.

WO 2006/065754 A2 describes a sensor dispenser which is set up to determine an analyte concentration in a body fluid. In this case, a cap of the instrument holds a cartridge with test strips, wherein calibration information from the cartridge can be transmitted to the instrument. In addition, the instrument comprises a lancet apparatus.

It is therefore an object of the present invention to provide a medical system and a method for monitoring a medical system which avoid the drawbacks of known medical systems and methods for monitoring such systems. In particular, the medical system and the method are intended to allow a user to independently, easily, reliably and quickly identify replicated consumables.

SUMMARY

This object and others that will be appreciated by a person of ordinary skill in the art in view of this disclosure are achieved by a medical system and a method for monitoring such a medical system having the features of the independent patent claims. Advantageous developments of the invention, which can be implemented individually or in combination, are presented in the dependent claims. The wording of all claims is hereby made the content of this disclosure.

One concept of the present invention involves combining components which have hitherto acted largely independently of one another to form a medical system which contains a central control unit which can perform the aforementioned tasks of identifying consumables centrally. In this way, the central control unit used may be a measuring device which is present in the overall system anyway, for example, and which has its own "intelligence" (for example within the framework of a microcontroller) and which is therefore suitable for monitoring even independently functioning peripheral devices, such as lancing devices.

The invention accordingly proposes a medical system which comprises a central control unit and at least one invasive unit. The medical system may have been set up to perform one or more therapeutic tasks and/or diagnostic tasks and/or tasks involving sampling, for example. In particular, it may be a medical system which can be used for monitoring and treating diabetes patients, particularly in what is known as the home care sector. The medical system is thus made up of a plurality of components which comprise at least the central control unit and at least one invasive unit. These components may be functionally independent of one another, can be handled in decentralized fashion independently of one another, but may also be mechanically combined as a whole or in part, for example by means of a common housing, by means of connecting elements or the like.

The central control unit is set up to display at least one diagnostic measured value using a display element. By way of example, said diagnostic measured value can be ascertained by the central control unit itself, but can also be input into the central control unit externally. The central control unit therefore serves as an interface between a patient and the medical system. In this context, the central control unit used can comprise a measuring device which is present anyway in a medical system (for example a medical system for diagnosing and/or treating a diabetes patient). By way of example, the central control unit may accordingly have at least one measurement function for ascertaining a diagnostic measured value, for example an optical and/or electrochemical measurement function for ascertaining a blood glucose value, a lactate value, a cholesterol value or another analyte concentration in a sample of a body fluid. To perform said measurement function, the central control unit may have, by way of example, one or more test elements, for example test strips. Typically, said central control unit comprises data processing electronics, such as one or more microcontrollers, which are used to assist the display of the diagnostic measured value and which can also be used to perform data processing functions.

Thus in one embodiment the central measuring unit has at least one optical and/or electrochemical measuring unit which is set up to use at least one test element to ascertain a concentration for an analyte, particularly for a metabolite, in a body fluid. It will subsequently be assumed, without limiting the scope of the invention, that the central control unit comprises a blood glucose measuring device which can use a test strip or test tape with an appropriate test element and an optical and/or electrochemical measuring unit to ascertain a blood glucose concentration and can transmit said blood glucose concentration to a patient using a display element, for example in the form of a display.

Besides a central control unit defined in this manner, for which, as described above, a unit with its own "intelligence", i.e. for example with at least one microcontroller or another unit with means for performing computation operations, which is present in a medical system anyway is preferably used, the medical system also comprises at least one invasive unit. Said at least one invasive unit is functionally independent of the central control unit. In this context, "functionally independent" is intended to be understood to mean that the respective function of control unit and invasive unit can be performed independently of the presence of the respective other unit. In other words, the central control unit and the invasive unit are intended to be autonomous, that is to say to be functionally independent of one another. For the definition of the system term, reference can also be made to the description of FIG. 1 in the exemplary embodiments.

The invasive unit comprises at least one invasive consumable. The invasive unit as a whole and/or the invasive consumable is/are set up to invasively intervene in a tissue of a patient. In this context, "intervention" can be understood to mean perforation of the tissue, for example perforation of a skin part in order to obtain a sample of a body fluid, and/or it can be understood to mean temporary or permanent implantation of the invasive consumable, such as the introduction of a cannula or a subcutaneous sensor into a body tissue.

The invasive unit may generally have a peripheral device which interacts with the invasive consumable. The peripheral device and the invasive consumable can then jointly form the invasive unit. In this case, a peripheral device is generally intended to be understood to mean a device which is functionally independent of the central control unit and which is set up to (for example autonomously) ensure the operation of the invasive unit. Various examples of such peripheral devices are set out below.

The invasive unit may have a sampling function which can be implemented by a lancet, for example. Accordingly, the invasive unit may have a peripheral device in the form of a lancing device, for example, said lancing device being designed to perforate a skin part of a patient using a consumable in the form of a lancet.

Alternatively or in addition, the invasive unit may also have a medication function, for example, particularly a dosage function. Said medication function can be implemented in various ways. Thus, by way of example, the invasive unit may have a peripheral device in the form of a medication pen. The most common exemplary embodiments of such medication pens are insulin pens. Generally, such medication pens are designed to inject a dose of a medicament into a patient using a consumable in the form of a cannula. By way of example said dose can be preset and the dose can be administered by virtue of manual operation of the medication pen, for example by depressing a plunger.

Alternatively or in addition, the medication function may also be designed to be automated, for example using a peripheral device in the form of a medication pump. The most common exemplary embodiments of such mediation pumps are insulin pumps which automatically, for example over a previously defined period of time, supply a patient with a set dose of insulin. Generally, the medication pump is designed to inject a dose of a medicament using a consumable in the form of a catheter. In this case, the invasive consumable usually comprises a tube and a cannula which are able to be replaced and disposed of as a unit or else separately, for example.

Alternatively or in addition, the invasive unit may also comprise an analytical and/or diagnostic function. By way of example, the invasive unit may comprise a peripheral device in the form of a measuring unit, wherein the measuring unit is designed to use a consumable, which comprises a subcutaneous sensor which has been introduced into a body tissue of a patient, to ascertain a concentration of an analyte, particularly a metabolite, in a body fluid. In this case, the consumable may comprise not only a replaceable subcutaneous sensor, for example, but also supply lines, implantation aids or the like. It should be pointed out that the measured value delivered by said measuring unit can be independent of the measurement function of the central control unit, which is described above. By way of example, the measuring unit may be designed to perform measurements in the body tissue of a patient continuously over one or more days, whereas the central control unit is set up for isolated, measurements. By way of example, the central control unit with its measurement function can be used in order to perform a calibration measurement for the measured values delivered by a subcutaneous sensor.

It becomes clear from this description that the central control unit and the invasive unit are generally in completely functionally independent form; i.e. perform their respective functions independently of one another, even if said units may be connected to one another mechanically, for example. In one embodiment the invasive unit comprises the simplest design possible, i.e. does not have its own intelligence or electronics, for example. By way of example, the invasive unit may comprise pure mechanical functions (such as a purely mechanically operating lancing device), but these may also be in the form of electromechanical functions, for example. It is thus also possible for the lancing device to be driven electrically, for example, and/or for the medication function to be looked after by a pump or another form of actuator.

In all the described types of invasive units, at least one invasive consumable is therefore used. As described at the outset, said invasive consumable is a particularly critical point in the medical system, since the invasive properties of the consumable mean that the latter comes directly into contact with open body tissue of a patient. In this respect, sterility problems are particularly critically noticeable in the case of this consumable, said problems possibly arising, by way of example, when such consumables are used unduly often. Another problem is the problem of replication already addressed, since, by way of example, incorrectly packed, incorrectly stored or incorrectly manufactured consumables can likewise result in injury to the patient, with sometimes serious consequences for the health of the patient. A third problem is the interaction between the invasive consumable and the rest of the invasive unit, for example the peripheral device. In the case of replicas or incorrect manufacture of the consumable, there may be resultant damage to the invasive unit or other types of malfunction, for example, as described above.

Accordingly, it is proposed that the invasive unit be equipped with at least one contactlessly readable electronic identifier. In this respect, use is made of aspects of US 2004/0138688 A1, for example, but not using a simple optical bar code, rather electronically readable identifiers, that is to say identifiers which can be read even if there is no direct visual contact between the identifier and the reader. Examples of such electronic identifiers are set out in more detail below.

In contrast to the prior art, however, a separate reader is now not used to read the information in the electronic identifier, but rather the invention involves the central control unit being set up to electronically read the at least one piece of information in the electronic identifier. By way of example, it is thus possible for the central control unit to be designed to have an appropriate interface for reading the electronic identifier, for example an interface which is set up to send and/or receive electromagnetic waves, for example in the radio-frequency range.

Hence, the medical system based on the present invention differs fundamentally from systems in which electronic identifiers are used in order to render the system serviceable. In contrast to US 2006/0182656 A1, for example, in which the insertion of a test strip from a test strip dispenser involves batch information from the test strip being transmitted to a measuring device, without which information the measuring device would not be able to perform its function, the invasive unit and the central control unit operate independently of one another in the present case. The central control unit merely additionally performs the task of reading the at least one piece of information and, as set out in more detail below, keeping it for further use. The concept of the present invention also differs from EP 1 352 611 A1, for example, in the same way.

The advantage of the inventive configuration of the medical system is that there is now information available centrally in an independent controller about the at least one invasive unit used. Said at least one piece of information is transmitted without it requiring any contact between the central control unit and the invasive unit. The consumables are therefore intended for devices which can be operated independently of the central control unit and which, by way of example, do not have to contain their own electronic reading capabilities for the piece of electronic information in the identifiers. In this way, it is firstly possible to dispense with separate readers for electronic identifiers, and the invasive units themselves, or the peripheral devices, can be kept for calculation in a technically simple fashion and optionally without their own electronics or microcontrollers. In addition, there is nevertheless information available centrally in the central control unit about the invasive units or the invasive consumables. This is of particular significance, since the medical system as a whole, if also implemented by functionally independent units, is intended to perform a common medical task, such as the diagnostic and/or therapeutic care of a patient with a particular clinical picture, particularly a diabetes patient. This centrally available piece of information can, as set out in more detail below, be used beneficially in various ways.

By way of example, the central control unit may be set up to take the piece of information which is read as a basis for transmitting an audible cue and/or a visual cue and/or a haptic cue, particularly a vibration, to the user. In this way, by way of example, the user may be provided with a piece of information about whether a consumable has been inserted in the invasive unit, whether it is correctly positioned and/or oriented, and there may even be a positioning aid provided. This is of great advantage in patients with visual impairments, for example, which frequently occurs in diabetes patients.

The piece of information which can be electronically read contactlessly may comprise at least one of the following pieces of information, for example:
  a piece of information about the manufacturer of the invasive unit and/or of the peripheral device and/or of the invasive consumable;
  a piece of information about a date of manufacture of the invasive unit and/or of the peripheral device and/or of the invasive consumable;

a piece of information about the type of the invasive unit and/or of the peripheral device and/or of the invasive consumable, particularly a batch number;

an individual serial number;

a number of invasive consumables contained in the invasive unit;

an expiry date for the invasive unit and/or for the peripheral device and/or for the invasive consumable.

As described above, the invasive unit may have not only the invasive consumable but additionally at least one peripheral device which interacts with the invasive consumable. There may also be a plurality of invasive consumables combined in the invasive unit, for example in a consumables magazine. In this context, a "consumables magazine" is intended to be understood to mean all usual types of containers which comprise more than one invasive consumable. Examples which may be cited in this context are drum magazines, bar magazines, line magazines, zigzag magazines, cassette tapes or the like. One invasive unit may also comprise different types of invasive consumables, for example different types of lancets, or may comprise invasive and noninvasive consumables, for example lancets and simple test elements.

When a peripheral device is used, the at least one electronic identifier may be connected to the at least one invasive consumable, for example, or may, alternatively or in addition, also be connected to the peripheral device. In one embodiment, the invasive consumable may comprise at least one first contactlessly readable electronic identifier for storing at least one first piece of information, for example, and the peripheral device may comprise at least one second contactlessly readable electronic identifier for storing at least one second piece of information. This allows operational reliability to be increased, for example, by virtue of the central control unit reading the first piece of information and the second piece of information at the same time or with a time lag. By way of example, it is thus possible to ascertain whether a correct consumable is used in combination with a correct peripheral device, and if necessary a warning can be output to a user if this is not the case. The central control unit may accordingly be set up to read the at least one first piece of information and the at least one second piece of information. Both pieces of information can be compared with target information (for example a first piece of target information and a second piece of target information), for example.

Further exemplary embodiments relate to the use of the at least one piece of information by the central control unit. By way of example, the piece of information can be stored for a later evaluation, for which purpose the central control unit can provide a volatile and/or nonvolatile data memory and/or a database, for example. The at least one piece of information can also be evaluated in the case of error diagnosis, for example within the context of a customer complaint. In addition, the at least one piece of information can be provided for a user, for example by means of the display element described above. Said at least one display element may comprise one or more displays, for example matrix displays, or segmented displays and/or also simpler display elements, for example. It may comprise simple symbols or luminous fields or luminous dots, for example. Other types of display are also possible, for example as described above audible or haptic signals. By way of example, if the information differs from a target value or target range, a warning can be output to a user and/or a piece of warning information can be stored in a data memory. It is thus possible for a "flag" to be set, for example, if an unsuitable, i.e. for example unauthorized, erroneous or replicated consumable is used. This flag can be read later as appropriate. In addition, if a discrepancy from a target value or a target range is found, it is also possible to actively disable at least one device function of the central control unit, so that erroneous operation of the overall medical system is prevented, for example. In addition, it is also possible to ascertain when the invasive consumable in the invasive unit was last changed. Accordingly, warnings can be output, for example, if the last change is more than a prescribed period of time in the past, and/or changes of the consumable can be initiated in another way, and/or system functions can again be actively disabled. In addition, the at least one piece of information can also be used to ascertain a manufacturer of the invasive unit and/or of the invasive consumable, for example. This piece of manufacturer information can in turn be output, for example, or can in turn be stored for later evaluation. Alternatively or in addition, the piece of information can also be used for preventing replication, for example, particularly for protecting against use of replicated invasive consumables, such as lancets, test strips or the like. Such replicas are not only able to cause financial loss but can also impair the functionality of the overall medical system, which can have fatal consequences for a user and patient. Various other options are conceivable and are explained in more detail in the course of the description of an embodiment of a useful method below.

As described above, the central control unit in one embodiment comprises an interface for interchanging the piece of information with the identifier. Usually, however, a plurality of such interfaces are required, since there is not only communication with the at least one identifier but also communication with external data processes devices, for example. Thus, the central control unit may comprise at least one first interface for data interchange with an external data processing device and also at least one second interface for interchanging the one piece of information described above with the at least one identifier. This development of the invention allows for the fact that many central control units today, for example blood glucose measuring devices, already have communication interfaces which can be used to communicate with an external computer, for example. These interfaces may be in the form of wired interfaces, for example, and/or in the form of wireless interfaces, such as Bluetooth interfaces and/or infrared interfaces. In addition to this first interface, the central control unit accordingly may additionally comprise the at least one second interface, which is an interface for contactless electronic data interchange with the at least one identifier, which is naturally matched to the configuration of the at least one identifier.

Further advantageous configurations of the invention relate to the configuration of the at least one identifier used. Typically, said identifier is a purely passive identifier which dose not comprise its own power supply. By way of example, this can be implemented by using an electronic bar code, as described in WO 2004/088037 A1, for example. Said electronic bar code involves bar code strips being applied as electrically conductive strips which can be read contactlessly via antennas in a reader. RFID chips also usually have no power supply of their own and draw their power from the received electromagnetic radiation.

In addition, a variable identifier can also be used, that is to say an identifier in which the written piece of information can be altered externally. This can be done in the case of an electronic bar code, for example, by acting upon the bar code itself, for example by destroying individual strips of the bar code. Other types of variable identifiers are also known, such as radio-frequency identifiers (RFID chips). In the case of these radio frequency identifiers, which may be produced with a silicon chip and an antenna and/or an organic electronic circuit, for example, it is possible for an appropriate write operation, for example, to be used to write information in a targeted manner by injecting an electromagnetic field. For reading purposes, such identifiers usually use the externally injected power in order in turn to emit the requested piece of information via one or more antennas. Such radio frequency chips are known from various areas of technology.

In addition, the at least one identifier may be in a form such that it also comprises a piece of information about a position and/or orientation of the invasive consumable within the invasive unit, for example within the peripheral device. This can be implemented when an identifier is used on a peripheral device and for the use of identifiers on the consumables, for example, by determining the relative position of the identifiers relative to one another. Examples of this configuration are cited in more detail below.

Besides the medical system in one of the embodiments described above, the invention also proposes a method for monitoring a medical system. The medical system is in turn intended to be a medical system which can be self contained in as much as it is used for monitoring and/or diagnosis and/or therapy for one or more complete clinical pictures, such as for the care of diabetes patients. In particular, said medical system may be a medical system according to one of the embodiments described above, so that for exemplary embodiments and definitions of system components it is possible to refer to the description above, for example.

Again, the medical system comprises a central control unit, which is set up to display at least one diagnostic measured value using at least one display element, and at least one invasive unit with at least one invasive consumable, which can invasively intervene in a tissue of a patient. The invasive unit again comprises at least one contactlessly readable electronic identifier for storing at least one piece of information. The method is set up such that the central control unit reads the at least one piece of information in the electronic identifier.

In its embodiment variants, the method relates particularly to how the at least one piece of information in the at least one identifier is evaluated. The text below describes the various options, which can also be used in combination, with the respective emphasis being on the evaluation. Naturally, the evaluated information can also be stored in one more data memories and/or databases. For later evaluation, said information can be transmitted to a user, for example visually and/or audibly and/or haptically, and/or can be transmitted to an external computer (for example a doctor's computer or a company computer of the manufacturer in the case of a flawed diagnosis or misdiagnosis) or can be used further in another way.

By way of example, the central control unit can use the piece of information to ascertain whether the invasive consumable has already been used previously in the medical system, for example in combination with a measuring device. This piece of information can be used several times, for example in order to provide a patient with product information or use information upon first use. Alternatively or in addition, it is also possible to avoid multiple use, for example, in order to avoid sterility problems.

Alternatively or in addition, the central control unit could also use the transmitted piece of information to ascertain whether an expiry date for the invasive unit and/or for the invasive consumable has lapsed. In response to this ascertainment, it is again possible to output a warning to a user, for example, or it is also possible to trigger an action, in this case as in other cases, such as disabling a system function of the medical system. In this case, as in other cases, the piece of information can also be stored for later evaluation in one or more data memories, for example volatile or nonvolatile data memories, in the central control unit. This piece of information is available later, for example, for further evaluation, presentation, error diagnosis or as a supplementary piece of information for a medical diagnosis. The piece of information can be evaluated particularly in the course of error diagnosis and/or handling of a complaint.

Alternatively or in addition, the method may also be in a form such that the central control unit uses the piece of information to ascertain whether the invasive unit and/or the invasive consumable is/are suitable for use in the medical system. By way of example, this allows recognition of whether a consumable material authorized by the manufacturer of the system or of individual system components (such as peripheral devices) is involved or replicas or imitations. As described above, this functionality option not only has considerable financial significance for the system manufacturers but can also make a substantial contribution to avoiding malfunctions or destruction of the medical device, to preventing incorrect diagnostic results or even to avoiding infections or injuries as a result of incorrectly manufactured and/or stored consumables. Accordingly, this piece of information can in turn be stored in purely passive form in the central control unit and/or can be presented for a patient or a doctor and/or can be kept ready for later evaluation, and/or it is also possible to actively disable system functions, for example, in order to avoid malfunctions from the outset.

In addition, the method may also be in a form such that the central control unit uses the piece of information to ascertain how many invasive consumables the invasive unit comprises. By way of example, this makes it possible to ascertain a total number of lancets in a magazine of the invasive unit. This can be displayed to a user, for example. The number of unused invasive consumables, such as the number of unused lancets, can also be ascertained. This can be done—as described above by using a variable identifier, for example, wherein, by way of example, any use of an invasive consumable involves the identifier being altered by the central control unit and/or by the invasive unit itself, for example by a peripheral device. In the former case, it is possible to alter a piece of information stored in a radio-frequency chip, for example, and in the latter case, it is possible, by way of example, to mechanically alter an electronic bar code, for example by removing or adding individual bars or other forms of segments of this bar code.

In addition, the central control unit can ascertain whether the invasive consumable has already been used. If this is the case, a user can be asked to use a new invasive consumable and/or it can be ensured that the invasive unit uses a new invasive consumable. Again, the evaluated piece of information can therefore be used purely passively, that is to say can be stored, for example, can be transmitted to a user by an appropriate display, or an active system function can be initiated or disabled.

If the identifier is designed such that the piece of information stored in said identifier can be changed, for example by the central control unit and/or a peripheral device, it is also possible to store a piece of information about the identity of the central control unit in the identifier. In this way, following recognition of an identifier by the central control unit, for example, it is possible for a measuring device, a serial number for the central control unit or a serial number for the measuring device to be stored in said identifier, for example. If this serial number or other form of information about the identity of the central control unit is subsequently read in by the same central control unit or another central control unit used later, each of the measuring devices can recognize that this is a used invasive unit or used invasive consumable. This piece of supplementary information can in turn be stored and/or displayed, for example, and specific actions can be initiated, such as disabling system functions, if a consumable authorized by the manufacturer of the medical system has not been inserted, or the invasive unit has been used previously with another central unit.

In addition, particularly when a position-sensitive identifier is used, it is also possible to recognize whether the invasive consumable is correctly positioned in the invasive unit. In this context, it is even possible to use the central control unit to effect user guidance to the extent that signal tones and/or vibrations from the central control unit are output while the consumable is inserted into a peripheral device. These signal tones or vibrations can alter in volume or frequency, for example, when a visually impaired user inserts the consumable into the peripheral device, so that this operation can be aided by virtue of the provision of audio queues. Alternatively or in addition, it is also possible to provide an indication of confirmation that the consumable material has been inserted correctly. In a further aspect of the method, the central control unit can use the piece of information to ascertain when the last change of invasive consumable took place. By way of example, the date of the last change can in turn be stored for later evaluation and/or can be output to a user. In addition, it is also possible to initiate actions, such as a warning function, when a change of consumable is required and/or a blocking function when the last change is more than a prescribed period of time in the past. In principle, it would also be possible to store the number of uses for the consumables used.

In addition, if the invasive consumable comprises at least one lancet which interacts with a peripheral device in the form of a lancing device, it is possible for the central control unit to use a piece of information to also ascertain what depth of prick is set on the lancing device. This can be achieved, by way of example, by virtue of the identifier in turn being in the form of a variable identifier, with alteration of the depth of prick comprising alteration of the readable piece of information stored in the identifier. The depth of prick can be displayed, stored or used otherwise, for example.

It should be pointed out that the medical system described above can be set up to support the illustrated method in one of the embodiment variants described. By way of example, it is thus possible for the central control unit to be set up to perform the method in one or more of the illustrated variants. By way of example, the central control unit may to this end—as described above—comprise one or more microcomputers which assist the ascertainment and/or storage and/or evaluation of one of the cited pieces of supplementary information by means of appropriate program-based devices and/or software, for example, and/or are set up to take this supplementary information as a basis for performing further actions, for example the disabling of one or more system functions of the medical system, as described above.

The method described above and the medical system in one of the described embodiments provides the manufacturer of the medical system or of individual components of the medical system with the particular advantages that the patients can replace the consumables in due time, since they are reminded of the date of the last change by the central control unit, for example. This may be of financial significance, since peripheral devices and measuring devices are usually system components which are sold without covering costs, whereas the consumable material represents the components which are actually of financial interest. In addition, the method and the proposed system afford unique selling points in the face of possible competitors. Furthermore, the imitation of consumables, particularly lancets, is made significantly more difficult, since the customers are now able to recognize unauthorized consumables independently. This makes it possible to avoid or reduce the loss of image which can arise as a result of replicas.

For the patient, the particular advantages arise that he can be reminded of a time for a change of consumable by virtue of the display of the date of the last change of consumable, for example. This increases the user-friendliness of the medical system. In addition, for blood sugar measurement, for example, he can see at a glance how many consumables, for example lancets, are still available to him for further measurements. Recognizing that authorized or unauthorized consumables are being used also provides certainty for the patient. In addition, the possibility of recognizing whether consumables have been inserted into the peripheral devices correctly provides additional operational reliability. To protect the patient, it is also possible, if needed, for example in a clinic mode, to ensure that a consumable—for example a lancet—can be used only once.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

A medical system 110 subsequently denotes a central control unit 114 and an invasive unit 120, which are generally functionally independent of one another, such that the respective function of the central control unit 114 and of the invasive unit 120 can be performed independently of the presence of the respective other unit 114, 120. This means that the central control unit 114 has one or more functions which can be used by the user without the presence of the invasive unit 120 and conversely that the function of the invasive unit 120 can be used by the user without there being a need for the central control unit 114 to be present for this purpose.

Figure 1:
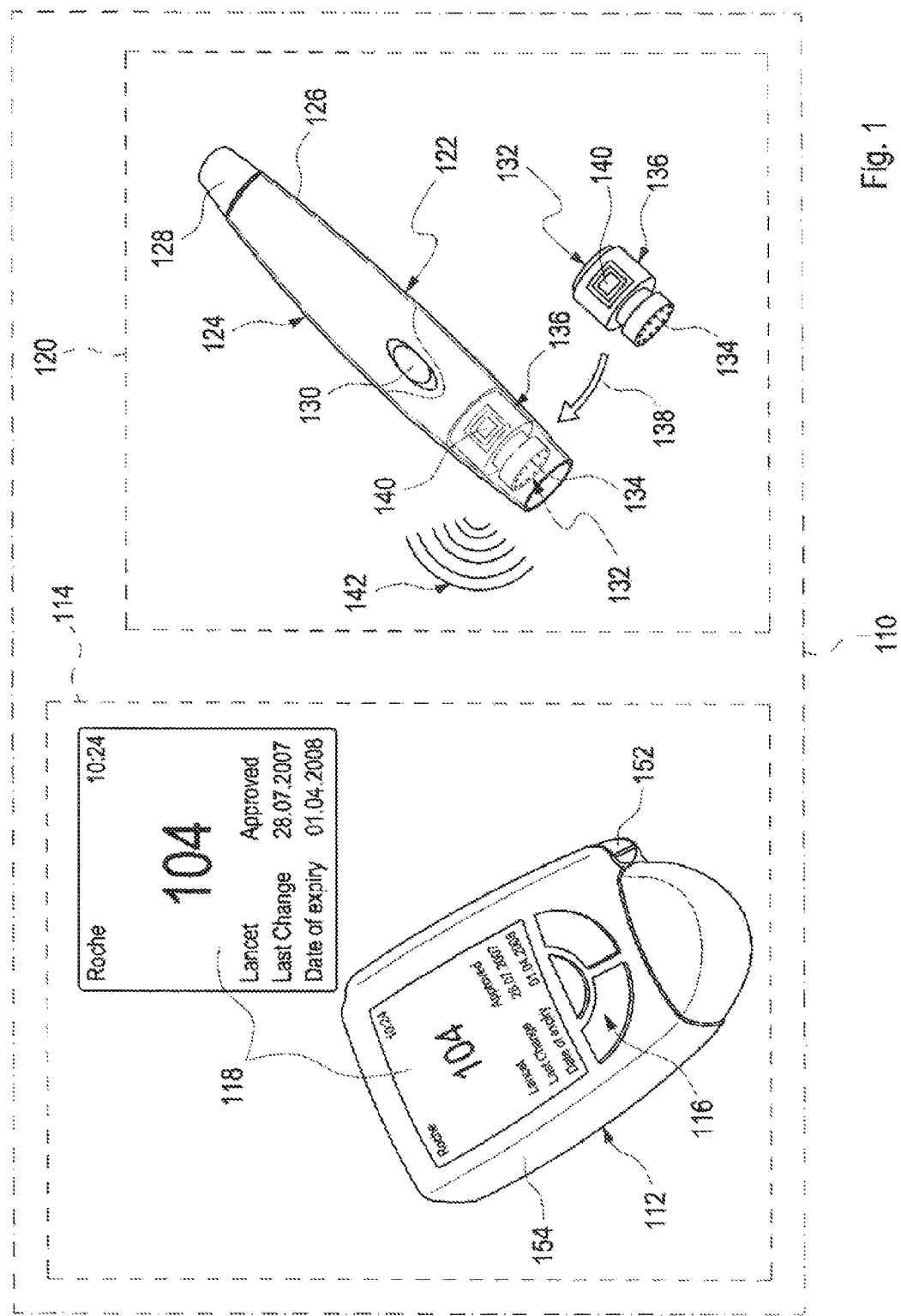
FIG. 1 shows an exemplary embodiment of a simple medical system for controlling diabetes.

FIG. 1 shows a first, simple exemplary embodiment of a medical system 110. This is a medical system 110 which can be used for controlling diabetes and which, in this exemplary embodiment, comprises two individual components which can, in principle, be used independently of one another. Thus, the medical system 110 first of all comprises a measuring device 112 which acts as a central control unit 114 in the medical system 110. In the exemplary embodiment shown here, the measuring device 112 is a blood glucose measuring device, for example, which can use a test element (not shown in FIG. 1) and, by way of example, an optical and/or electrochemical measurement method to ascertain a blood glucose concentration in a droplet of blood. The measuring device 112 has operator control elements 116 for controlling the system functions, actuation and evaluation electronics (not shown in FIG. 1) for evaluating the test strip measurement and a display element 118, which, for the purpose of clarification, is shown again in an enlarged illustration in FIG. 1 to the right of the measuring device 112. In addition, the measuring device 112 may comprise additional components, such as one or more interfaces, a magazine for holding test elements or the like.

As a second component, the medical system 110 shown in FIG. 1 comprises an invasive unit 120, which in this exemplary embodiment is designed to perform a sampling function for obtaining a liquid sample, particularly a droplet of blood. In this respect, the function of the invasive unit 120 is independent of the function of the measuring device 112, even if these as a whole form the medical system 110 for controlling diabetes.

The invasive unit 120 comprises a peripheral device 122 in the form of a lancing device 124. The lancing device 124 has a spring mechanism which is arranged inside a housing 126 and which can be tensioned by means of a tensioning knob 128 and can be released by means of a release knob 130.

Furthermore, the invasive unit 120 in this exemplary embodiment comprises a plurality of invasive consumables 132, which in this exemplary embodiment are in the form of lancets 134. The lancets 134 are combined in a drum-like magazine 136, each of said lancets 134 being arranged in a separate lancet chamber. The magazine 136 is inserted into the housing 126 of the lancing device 124, so that one lancet 134 can be used for each lancing operation. By way of example, the magazine 136 shown may be a commercially available magazine of Accu-Chek Multiclix Safety Drum type. In this case, FIG. 1 shows the magazine 136 once in the uninstalled state and once in the state which has been inserted into the lancing device 124, the operation of insertion being denoted symbolically in FIG. 1 by the arrow 138.

Furthermore, the invasive consumables 132 in the exemplary embodiment shown in FIG. 1 are equipped with an identifier 140. In FIG. 1, this identifier 140 is shown only symbolically and in this case is symbolized as an RFID chip. This identifier 140 can therefore be read electronically and is capable of storing at least one piece of information. This piece of information can be requested or read from the measuring device 112 contactlessly by electronic means, which is denoted symbolically in FIG. 1 by the reference numeral 132. By way of example, this electronic information transmission can be effected by radio waves, for example radio waves in the megahertz or gigahertz range, as is customary for such identifiers 140.

Furthermore, it should be pointed out that in the exemplary embodiment shown in FIG. 1 a single identifier 140 is attached to the magazine 136. In this respect, a distinction is subsequently not drawn between the invasive consumables 132 combined in the magazine 136 in the form of the lancets 134 and the magazine 136 itself. However, it should be pointed out that the individual lancets 134 or invasive consumables 132 may also be respectively marked, for example in similar fashion to the lancet marking, which is shown in US 2004/0138688 A1, but using electronically readable identifiers. Combinations of these configurations are also conceivable, that is to say a configuration in which all the invasive consumables 132 are produced with identifiers and in which additionally the magazine 136 has an identifier 140 of this kind. In addition, the lancing device 134 itself may also have an identifier 140—as described above.

In this way, the central control unit 114 can recognize, by way of example, that a lancing device 124 and/or invasive consumables 132 are in a reading range. In addition, it is possible to recognize what types of consumables 132 are involved, which allows new functions and prevention of replication. For these new functions, reference is made by way of example to the description above. As an example, FIG. 1 shows that the measuring device 112, for example, recognizes that authorized consumables 132 are involved. This can be used for an appropriate display on the display element 118, for example, as indicated symbolically in FIG. 1 ("Lancet approved"). In addition, the date of the last change of consumable can be displayed ("last change") and an expiry date ("date of expiry") for the consumable can be displayed. Further possible exemplary embodiments are set out in the description above.

Figure 2:
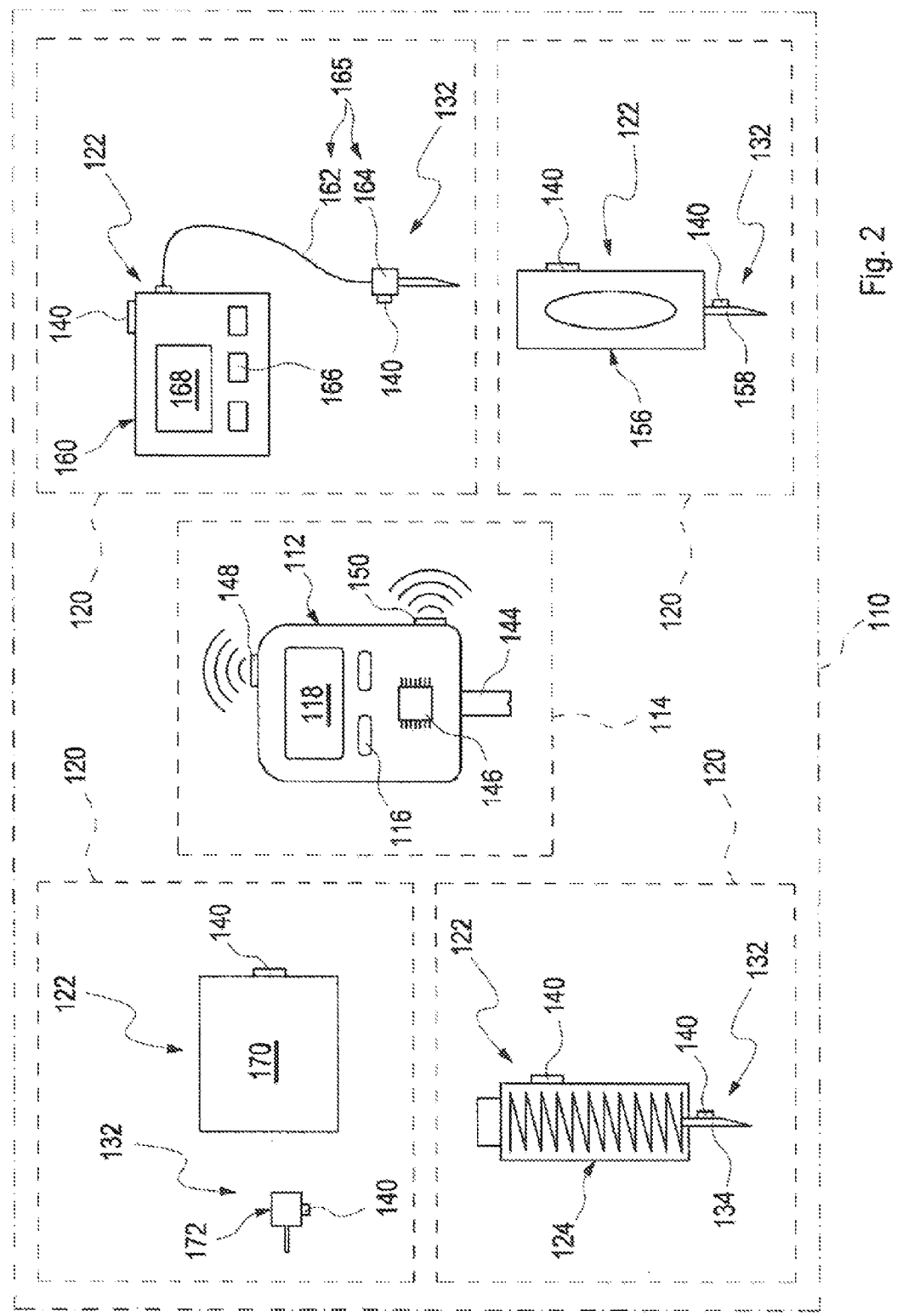
FIG. 2 shows a basic outline of an expanded medical system with a plurality of invasive units.

FIG. 2 symbolically shows an expansion of the medical system 110 described above. In this case, the medical system again comprises a central control unit 114 in the form of a measuring device 112. The measuring device 112 may be in similar form to that described for FIG. 1, for example, may have a display element 118 and an operator control element 116, and may be designed, by way of example, to use a test strip 144 or to use a test element produced in another way (for example a test ribbon) to determine an analyte concentration, for example blood glucose concentration, and to present it as a diagnostic measured value on the display element 118.

In addition, FIG. 2 symbolically shows a data processing device 146 which can be used, by way of example, for electronically processing diagnostic measured values and/or for performing other system functions (such as the evaluation of the information transmitted by the identifier 140). Furthermore, the measuring device 112 in the exemplary embodiment shown in FIG. 2 has two interfaces, which are merely shown symbolically. A first interface 148 is used for data interchange with external devices, for example external computers. Said first interface 148, which may be in the form of an infrared interface, for example, can therefore be used, by way of example, to perform software updates on the measuring device 112 and/or to transmit medical measurement data to an external computer (for example a doctor's computer and/or a patient's computer). In addition, the measuring device 112 has a second interface 150, which can be used to request information, which is stored in identifiers 140 of the invasive unit 120, contactlessly and by electronic means. This second interface 150 can comprise a radio interface. However, both interfaces 148, 150 may also be combined to form a single interface.

FIG. 2 symbolically shows the central control unit 114 as a self-contained unit by means of the dashed line. This is intended to symbolize that this self-contained unit can operate independently in terms of function, but said functional unit 114 may also have further associated components, such as a dispenser box for providing test strips 144 or similar components.

Besides said central control unit 114, the medical system 110 in the example shown in FIG. 2—in contrast to FIG. 1—comprises four invasive units 120. These invasive units 120 are generally independent of the central control unit 114 in terms of function and may also be independent among one another. This functional independence, which is illustrated by the dashed line 114, does not mean that these components cannot be arranged in physical proximity to the central control unit 114, however. This becomes clear from FIG. 1, in which it is possible to see, on the measuring device 112, a coupling point 152 by means of which the lancing device 124 can be coupled to a housing 154. In this coupled state, although the central control unit 114 and the invasive unit 120 in the form of the lancing device 124 form a mechanically combined system, the system functions of the central control unit 114 (measurement and display) and of the invasive unit 120 (sampling) continue to be clearly separate.

In the medical system 110 in FIG. 2, the invasive units 120 again comprise a lancing device 124 as a peripheral device 122, which interacts with invasive consumables 132 in the form of lancets 134. For a description of the lancing device 124, it is largely possible to refer to FIG. 1.

In addition, the medical system 110 comprises an invasive unit 120 in the form of a peripheral device 122 in the form of an insulin pen 156. In FIG. 2, said insulin pen 156 is merely shown symbolically and interacts with an invasive consumable 132 in the form of a cannula 158. The insulin pen 156 is designed to allow a patient to be injected with a preset amount of insulin medication.

In addition, the medical system 110 comprises a peripheral device 122 which is in the form of an insulin pump 160 and which interacts with a consumable 132 in the form of a tube 162 and a cannula 164. The tube 162 and the cannula 164 are usually in the form of a common, disposable unit, which is denoted as a catheter 165 in FIG. 2. The insulin pump 160 therefore allows a pump (not shown in FIG. 2) to be used to supply a patient from a storage vessel with an amount of insulin which is preset by means of operator control elements 166 and which is shown on a display element 168.

As a fourth invasive unit 120, the medical system 110 comprises a peripheral device 122 in the form of a measuring unit 170 which interacts with a consumable 132 in the form a subcutaneous sensor 172 in order to ensure continuous Monitoring of a blood glucose value, for example, in tissue layers of a patient.

It should be pointed out that the invasive units 120 shown in FIG. 2 have merely been selected by way of example on the basis of customary components which are used in diabetes monitoring. Naturally, the medical system 110 may also comprise further or other types of component, however.

In the exemplary embodiment shown in FIG. 2, both the invasive consumables 132 and the peripheral devices 122 are respectively produced with electronic identifiers 140. As described above, however, another configuration is also possible, for example by virtue of exclusively the invasive consumables 132 or the peripheral devices 122 being equipped in this manner. The second interface 150 can therefore be used by the central control unit 114 to request information from said electronic identifiers 140.

As identifiers 140, very inexpensive and small variants of electronically readable identifiers come predominantly into question. The information in the identifiers 140 should be readable when the invasive units 120 are in proximity to the measuring device 112, for example when the lancing device 124 is coupled to the measuring device 112 or its connected thereto. However, it is also conceivable to be arranged in physical proximity, for example at a distance of less than 50 cm.

Examples of suitable electronic identifiers 140 are RFID chips from Hitachi in Japan, which have silicon chips with dimensions of less than 0.4 mm edge length including the antenna. Typical operating frequencies in this case are 2.45 GHz, with storage capacities of 128 bits. Such RFID chips are potentially extremely inexpensive, since they were originally developed for use in bank notes. Furthermore, RFID chips of "mic3®TAG" type from microsensys GmbH, Germany, for example, also come into question, said chips having edge lengths of approximately 1.6 mm☐1 mm, operating frequencies in the region of 13.56 MHz and storage capacities of 64 bits ROM. Other types of RFID chips can also be used, however.

As a further possibility for an exemplary embodiment of the identifiers 140, reference can be made to what is known as the "chipless identifier" from Acreo AB, Sweden. In this case, the stored piece of information is coded by means of a printed bar code comprising conductive ink (known as the HidE principle). This is an inexpensive method which can easily be integrated into previous product processes and in which approximately 10 to 30 bits of information can be put into the identifier 140 and read. The size of the storable information is in this case determined essentially by the size of the electronic bar code, that is to say particularly also by the size of the consumable 132.

Figure 3:
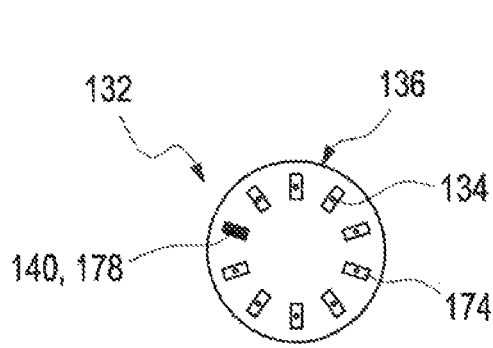
FIG. 3 shows a possible exemplary embodiment of the attachment of an identifier to a consumable.
Figure 4:
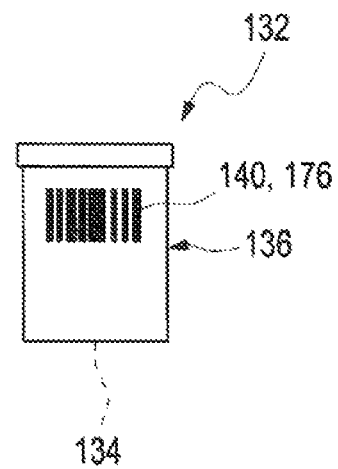
FIG. 4 shows an alternative exemplary embodiment, from that in FIG. 3, of the attachment of an identifier to a consumable.

The identifier 140 may be arranged on the invasive unit 120 in different ways. Examples of such arrangements and attachments are shown in FIG. 3 and FIG. 4. Thus, FIG. 3 shows an exemplary embodiment of invasive consumables 132 which are in turn in the form of lancets 134. In a similar manner to the exemplary embodiment in FIG. 1, these lancets are arranged in a drum-like magazine 136, the individual lancets 134 being arranged in lancet cavities 174. Said lancet cavities 174 are arranged in the drum magazine 136 so as to point radially outward in rotationally symmetrical fashion.

In this case, an arrangement has been chosen in FIG. 3 in which a lancet cavity 174 is not filled with a lancet 134. Instead, an identifier 140 is introduced into the lancet cavity 174 in this exemplary embodiment.

FIG. 4, by contrast, shows a magazine 136 in which an identifier 140 has been put onto the exterior wall of the magazine 136 from the outside. In contrast to FIG. 3, in which the magazine 136 is shown in plan view, FIG. 4 shows the magazine 136 in an illustration looking from the side. Whereas, in the embodiment shown in FIG. 3, an RFID chip 178 can be used as identifier 140, for example, the embodiment shown in FIG. 4 involves a conductive bar code 176 (chipless identifier) being printed, stuck or attached in another way onto the side wall of the magazine 136, and can comprise identifier 140. Various other configurations of the attachment of the identifier 140 are possible.

Figure 5:
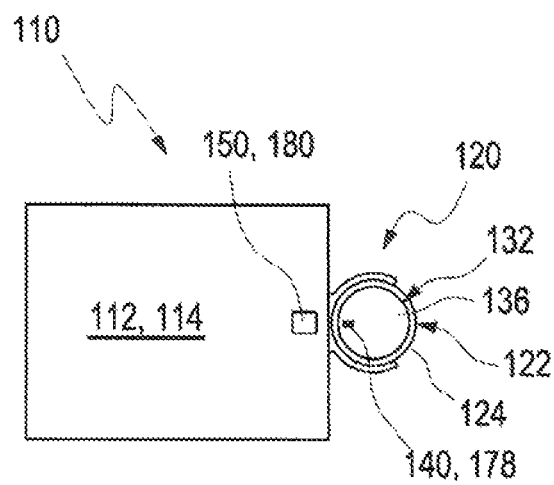
FIGS. 5A and 5B show a first exemplary embodiment of implementation of a position-sensitive identifier.
Figure 5:
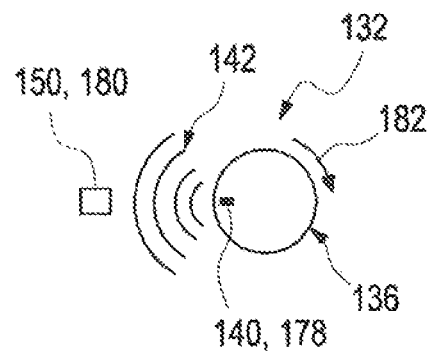
Figure 6:
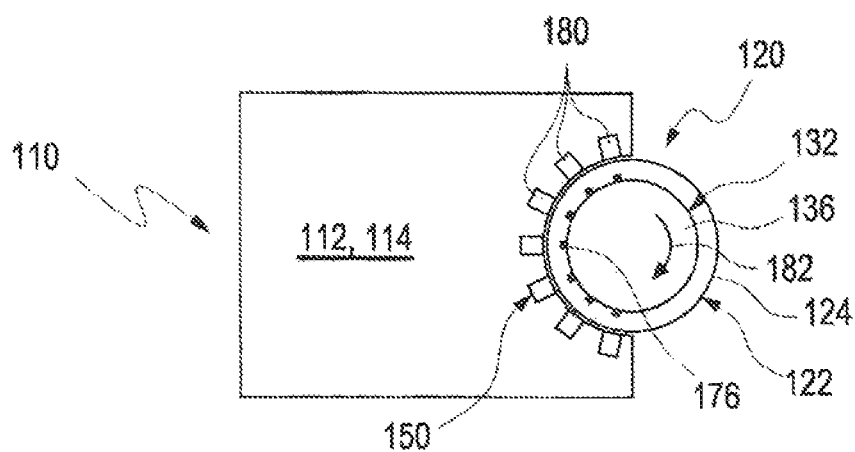
FIG. 6 shows a second exemplary embodiment of the implementation of a position-sensitive identifier.

FIGS. 5A to 6 show various options for reading the identifiers 140 using the central control unit 114. In this case, FIGS. 5A and 5B show an exemplary embodiment which corresponds to the medical system 110 shown in FIG. 1. In this case, the lancing device 124 in the exemplary embodiment shown is coupled to the measuring device 112, and the lancing device 124 contains invasive consumables 132 with a magazine 136. In the magazine, an RFID chip 178 as identifier 140 has been inserted into a lancet cavity 174 (not shown)—as shown in FIG. 3, for example. The measuring device 112 has a second interface 150 in the form of an antenna 180 which can be used to read the piece of information in the RFID chip 178. In this case, said second interface 150 may be in the form such that it not only requests the signal from the RFID chip 178 itself in terms of the content thereof but also registers a signal intensity.

Whereas FIG. 5A shows the entire medical system 110 symbolically, FIG. 5B merely shows a symbolic and highly simplified form of the case in which the magazine 136 rotates relative to the measuring device 112 (which is not shown in FIG. 5B). This rotation, which is denoted by the reference numeral 182 in FIG. 5B, attenuates the signal from the identifier 140 (denoted by the "reading" 142 in FIG. 5B). This attenuation can be registered by the measuring device 112, so that from this it is possible to infer a position for the identifier 140 and hence an angular position for the drum magazine 136. This case therefore involves a position-sensitive identifier 140 which is arranged asymmetrically on the consumables 132 or the magazine 136 therefor, so that the measuring device 112 can be used not only to read the piece of information in the identifier 140 but also to infer a positioning or orientation for the consumables 132 from the signal level or other signal properties.

FIG. 6 schematically shows another exemplary embodiment of a position-sensitive identifier 140. Again, the medical system 110 shown corresponds to the medical system 110 shown in FIG. 1, for example, so that it is again possible to refer to the description above.

In this exemplary embodiment, however, the identifier 140 corresponds to the exemplary embodiment shown in FIG. 4 and comprises a conductive bar code 176 fitted to the perimeter of the magazine 136. The second interface 150 of the measuring device 112 comprises a plurality of individual antennas 180, which altogether can determine the positioning of the strips or areas of the conductive bar code 176. In a similar manner to the plate capacitors, an electrical field between said antennas 180 and the strips of the conductive bar code 176 changes, for example, which can be used to determine the positioning of the magazine drum 136. When the magazine 136 is rotated (reference numeral 182 in FIG. 6), the signal on said second interface 150 alters, from which it is again possible to infer the orientation of the consumables 132.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A medical system comprising a central control unit configured to display a diagnostic measured value using a display element and an invasive unit comprising an invasive consumable, wherein the invasive consumable is configured to invasively intervene in a tissue of a patient, wherein the invasive unit has a contactlessly readable electronic identifier for storing a piece of information, wherein the central control unit is set up to electronically read said piece of information in the electronic identifier and perform an action responsive to said piece of information, wherein the central control unit and the invasive unit are functionally independent of one another such that the central control unit has a function which can be used by the user without the presence of the invasive unit and conversely the function of the invasive unit can be used by the user without the need for the central control unit to be present for this purpose, the respective function of the central control unit and of the invasive unit being capable of being performed independently of the presence of the respective other unit, wherein the central control unit has a measuring unit which is set up to use at least one test element to ascertain a concentration of an analyte in a body fluid, wherein the measuring unit is selected from the group consisting of an optical measuring unit and an electrochemical measuring unit.

2. The medical system as claimed in claim 1, wherein the invasive unit has a function selected from the group consisting of: a lancet function; a dosage function; an analytical function which is functionally independent of the measurement function of the central control unit; and a diagnostic function which is functionally independent of the measurement function of the central control unit.

3. The medical system as claimed in claim 2, wherein the invasive unit is configured to perform exclusively mechanical functions.

4. The medical system as claimed in claim 1, wherein the invasive unit further comprises a unit selected from the group consisting of: a peripheral device in the form of a lancing device, wherein the lancing device is designed to perforate a skin part of a patient using an invasive consumable in the form of a lancet; a peripheral device in the form of a medication pen, wherein the medication pen is designed to inject a dose of a medicament into a patient using an invasive consumable in the form of a cannula; a peripheral device in the form of a medication pump, wherein the medication pump is designed to inject a dose of a medicament into a patient using an invasive consumable in the form of a catheter; and a peripheral device in the form of a measuring unit, wherein the measuring unit is designed to use an invasive consumable comprising a subcutaneous sensor implanted in a body tissue of a patient, to ascertain a concentration of an analyte in a body fluid.

5. The medical system as claimed in claim 1, wherein the central control unit is set up to take the information read as a basis for transmitting a cue to the user, wherein the cue is selected from the group of cues consisting of: an audible cue; a visual cue; and a haptic cue.

6. The medical system as claimed in claim 1, wherein the information comprises one of the pieces of information selected from the group consisting of: a piece of information about a manufacturer of the invasive unit; a piece of information about a manufacturer of the peripheral device; a piece of information about a manufacturer of the invasive consumable; a piece of information about a date of manufacture of the invasive unit; a piece of information about a date of manufacture of the peripheral device; a piece of information about a date of manufacture of the invasive consumable; a piece of information about the type of the invasive unit; a piece of information about the type of the peripheral device; a piece of information about the type of the invasive consumable; an individual serial number; a number of invasive consumables contained in the invasive unit; an expiry date for the invasive unit; an expiry date for the peripheral device; and an expiry date for the invasive consumable.

7. The medical system as claimed in claim 1, wherein the invasive unit additionally has a peripheral device, wherein the peripheral device is set up to interact with the invasive consumable.

8. The medical system as claimed in claim 7, wherein the invasive consumable has a first contactlessly readable electronic identifier for storing a first piece of information, wherein the peripheral device has a second contactlessly readable electronic identifier for storing a second piece of information.

9. The medical system as claimed in claim 8, wherein the central control unit is set up to read the first piece of information and the second piece of information.

10. The medical system as claimed in claim 8, wherein the central control unit is set up to compare the first piece of information with a first piece of target information and to compare the second piece of information with a second piece of target information.

11. The medical system as claimed in claim 1, wherein a plurality of invasive consumables are combined in a consumables magazine in the invasive unit.

12. The medical system as claimed in one of the preceding claims, wherein the action is selected from the group consisting of: storing for later evaluation; evaluating for error diagnosis; providing the piece of information for a user; outputting a warning to a user if the piece of information differs from a target value or target range; storing a piece of warning information in a data memory; disabling a device function of the central control unit if the piece of information differs from a target value or target range; ascertaining when the invasive consumable in the invasive unit was last changed; ascertaining a manufacturer of the invasive unit; and ascertaining a manufacturer of the invasive consumable.

13. The medical system as claimed in claim 1, wherein the central control unit comprises a first interface for data interchange with an external data processing device and wherein the central control unit comprises a second interface for interchanging the piece of information with an identifier.

14. The medical system as claimed in claim 13, wherein the identifier comprises a passive identifier without its own power supply.

15. The medical system as claimed in claim 1, wherein the electronic identifier comprises an identifier selected from the group consisting of: an electronic bar code; a variable identifier; a position-sensitive identifier for identifying a position of the invasive consumable within the invasive unit; a position-sensitive identifier for identifying an orientation of the invasive consumable within the invasive unit; and a radio-frequency chip.

16. A method for monitoring a medical system, comprising providing a medical system comprising a central control unit configured to display a diagnostic measured value using a display element and an invasive unit comprising an invasive consumable and a contactlessly readable electronic identifier for storing at least one piece of information; invasively intervening the invasive consumable in a tissue of a patient; reading the at least one piece of information in the electronic identifier with the central control unit and performing an action responsive to said piece of information; and functioning the central control unit and the invasive unit independently of one another such that the central control unit has a function which can be used by the user without the presence of the invasive unit and conversely the function of the invasive unit can be used by the user without the need for the central control unit to be present for this purpose, the respective functioning of the central control unit and of the invasive unit being performed independently of the presence of the respective other unit, wherein the central control unit has a measuring unit which is set up to use at least one test element to ascertain a concentration of an analyte in a body fluid, wherein the measuring unit is selected from the group consisting of an optical measuring unit and an electrochemical measuring unit.

17. The method as claimed in claim 16, wherein performing an action comprises using the central control unit to ascertain from the piece of information whether the invasive consumable has already been used previously in the medical system.

18. The method as claimed in claim 16, wherein performing an action comprises using the central control unit to ascertain from the piece of information whether an expiry date has lapsed, wherein the expiry date is selected from the group consisting of: an expiry date for the invasive unit; and an expiry date for the invasive consumable.

19. The method as claimed in claim 16, wherein performing an action comprises storing the piece of information for later evaluation in a data memory of the central control unit.

20. The method as claimed in claim 19, wherein performing an action comprises evaluating the piece of information in the course of one or both of an error diagnosis and a complaint.

21. The method as claimed in claim 16, wherein performing an action comprises using the central control unit to ascertain from the piece of information a suitability, wherein the suitability is selected from the group consisting of: a suitability of the invasive unit for use in the medical system; and a suitability of the invasive consumable for use in the medical system.

22. The method as claimed in claim 16, wherein performing an action comprises using the central control unit to ascertain from the piece of information how many invasive consumables the invasive unit comprises.

23. The method as claimed in claim 16, wherein performing an action comprises using the central control unit to ascertain from the piece of information how many unused invasive consumables the invasive unit comprises.

24. The method as claimed in claim 16, wherein performing an action comprises using the central control unit to ascertain from the piece of information whether the invasive consumable has already been used, and performing an action if it is ascertained that the invasive consumable has already been used, the action comprising one of prompting the user to use a new invasive consumable and ensuring that the invasive unit uses a new invasive consumable.

25. The method as claimed in claim 16, wherein performing an action comprises using the central control unit to store information about an identity of the central control unit in the identifier.

26. The method as claimed in claim 16, wherein performing an action comprises using the central control unit to ascertain from the piece of information whether the invasive consumable is correctly positioned in the invasive unit.

27. The method as claimed in claim 16, wherein performing an action comprises using the central control unit to ascertain from the piece of information when the last change of the invasive consumable occurred.

28. The method as claimed in claim 27, further comprising outputting a warning to a user if a maximum time since the last change of the invasive consumable has been exceeded.

29. The method as claimed in claim 16, wherein the invasive consumable comprises at least one lancet, wherein the invasive unit comprises a peripheral device in the form of a lancing device, wherein performing an action comprises using the central control unit to ascertain from the piece of information what depth of prick is set on the lancing device.

* * * * *